(12) United States Patent
Lee et al.

(10) Patent No.: US 8,802,662 B2
(45) Date of Patent: Aug. 12, 2014

(54) ANTI-HEPATITIS C COMPOSITION AND METHOD FOR PREPARING DRUG FOR INHIBITING HEPATITIS C VIRUSES OR TREATING HEPATITIS C

(75) Inventors: Lain-Tze Lee, Hsinchu (TW);
Shau-Feng Chang, Hsinchu (TW);
Hui-Ping Tsai, Hsinchu (TW);
Zong-Keng Kuo, Zhonghe (TW);
Chen-Fang Chung, Hsinchu County (TW)

(73) Assignee: Industrial Technology Research Institute, Hsinchu County (TW)

( * ) Notice: Subject to any disclaimer, the term of this patent is extended or adjusted under 35 U.S.C. 154(b) by 717 days.

(21) Appl. No.: 12/573,116

(22) Filed: Oct. 4, 2009

(65) Prior Publication Data
US 2010/0317637 A1 Dec. 16, 2010

(30) Foreign Application Priority Data
Jun. 16, 2009 (TW) ................. 98120040 A

(51) Int. Cl.
*A61K 31/58* (2006.01)

(52) U.S. Cl.
CPC ...................................... *A61K 31/58* (2013.01)
USPC ........................................................ 514/172

(58) Field of Classification Search
USPC ........................................................ 514/172
See application file for complete search history.

(56) References Cited

FOREIGN PATENT DOCUMENTS

| CN | 1273103 A | * | 11/2000 |
| CN | 1476829 A | | 2/2004 |
| CN | 1583020 | * | 2/2005 |
| CN | 101181567 A | | 5/2008 |

OTHER PUBLICATIONS

CN 1583020 abstract, 2005.*
Tada et al. "Limonoids from fruit of Melia toosendan and their cytotoxic activity," Phytochemistry, 1999, vol. 51, pp. 787-791.*
Liu et al. CN 1273103A abstract, 2000, CAPLUS, AN 2007:954128.*
First Examination Opinion Notice issued by the China Intellectual Property Office on Aug. 18, 2011, for the above-referenced application's counterpart application in China (Application No. 200910169270.4).
Wang et al., "Study of toosendanin intravenous injection agent", Chinese Herbal Medicines, 13(1), pp. 13-15, 20 (1982).
Takeya et al., "Cytotoxic Trichilin-Type Limonoids from Melia azedarach", Bioorganic & Medicinal Chemistry, vol. 4, No. 8, pp. 1355-1359 (1996).
Shi et al., "Toosendanin used as anti-tumor medicine, is separated from phloem of toosendan and purified", Database WPI Week 200437, Thomson Scientific, London, GB; AN 2004-390844.
Bartenschlager, "Hepatitis C virus replicons: potential role for drug development", Nature Reviews: Drug Discovery, vol. 1, 911-916, Nov. 2002, Nature Publishing Group.
Vrolijk et al, "A replicon-based bioassay for the measurement of interferons in patients with chronic hepatitis C", Journal of Virological Methods, 110, 201-209, 2003, Elsevier Science B.V.
Shi et al, "Biological effects of toosendanin, a triterpenoid extracted from Chinese traditional medicine", Progress in Neurobiology, 82, 1-10, 2007, Elsevier Ltd.
Zhou et al, "Limonoid Antifeedants From Melia Toosendan", Phytochemistry, vol. 41, No. 1, pp. 117-120, 1996, Elsevier Science Ltd.
Itokawa et al, "Cytotoxic Limonoids and Tetranortriterpenoids from *Melia azedarach*", Chem. Pharm. Bull. 43(7), 1171-1175, 1995, NII-Electronic Library Service.
Kiyomi Tada et al, "Limonoids from fruit of Melia toosendan and their cytotoxic activity", Phytochemistry 51, 787-791, 1999, Elsevier Science Ltd.
Lohmann et al, "Replication of Subgenomic Hepatitis C Virus RNAs in a Hepatoma Cell Line", Science, vol. 285, 110-113, 1999, www.sciencemag.org.
Office Action issued by the Japan Patent Office on Aug. 16, 2012, regarding the above-referenced application's counterpart application in Japan (Application No. 2010-105429).
Yuen et al., "Traditional Chinese medicine causing hepatotoxicity in patients with chronic hepatitis B infection: a 1-year prospective study", Alimentary Pharmacology & Therapeutics, 2006, vol. 24, p. 1179-1186.

* cited by examiner

*Primary Examiner* — Shengjun Wang
(74) *Attorney, Agent, or Firm* — Pai Patent & Trademark Law Firm; Chao-Chang David Pai

(57) ABSTRACT

The invention provides an anti-hepatitis C composition including: an effective amount of limonoid compound, wherein the structure of the limonoid compound is shown as Structure (I):

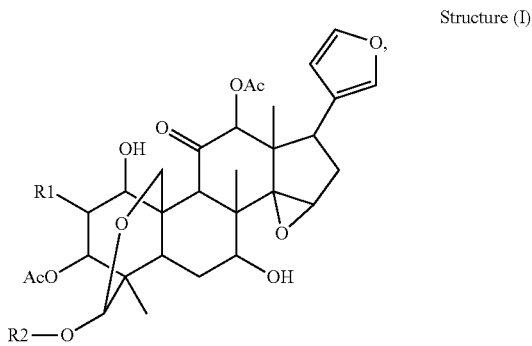

Structure (I)

where R1 comprises H or OAc and R2 comprises H or COCH$(CH_3)_2$; and a pharmaceutically acceptable carrier or salt, and the anti-hepatitis C composition is used for inhibiting hepatitis C virus or treating hepatitis C. The invention also provides a method for treating hepatitis C and a method for preparing a drug for inhibiting hepatitis C viruses or treating hepatitis C.

5 Claims, No Drawings

ANTI-HEPATITIS C COMPOSITION AND METHOD FOR PREPARING DRUG FOR INHIBITING HEPATITIS C VIRUSES OR TREATING HEPATITIS C

CROSS REFERENCE TO RELATED APPLICATIONS

This Application claims priority of Taiwan Patent Application No. 098120040, filed on Jun. 16, 2009, the entirety of which is incorporated by reference herein.

BACKGROUND OF THE INVENTION

1. Field of the Invention

The present invention relates to an anti-hepatitis C composition, and in particular, relates to a composition comprising a limonoid compound which may be used to inhibit hepatitis C viruses or to treat hepatitis C.

2. Description of the Related Art

According to recent estimates, about 2-3% of the world population is infected with hepatitis C and the number is increasing by 3-4 million patients every year. Presently, the only tested and approved anti-hepatitis C drug is α-interferon. Meanwhile, ribavirin has been used to enhance the anti-hepatitis C curative effect of α-interferon. However, use of both drugs induces serious side effects and results in drug-resistance in patients.

The basic illustrative structure of the limonoid compound comprises three 6-membered rings and a 5-membered ring connected to a furan ring by a single bond. The limonoid compounds mainly exist in plants of Rutaceae and Meliaceae. Toosendanin of limonoid compounds may be extracted from Melia toosendan Sieb. Et Zucc. Toosendanin is mainly used as a natural insecticide and is known to be capable of inducing apoptosis of human leukemia cells. Furthermore, toosendanin may also be extracted from chuanlianzi (fructus toosendan) which is mature, dried fruit of the Melia toosendan Sieb. Et Zucc and used as an herb for driving out roundworm and pinworm.

However, limonoid compounds being applied to effectively inhibit hepatitis C has yet to be disclosed.

BRIEF SUMMARY OF THE INVENTION

The invention provides an anti-hepatitis C composition, comprising: an effective amount of limonoid compound, wherein the structure of the limonoid compound is shown as Structure (I):

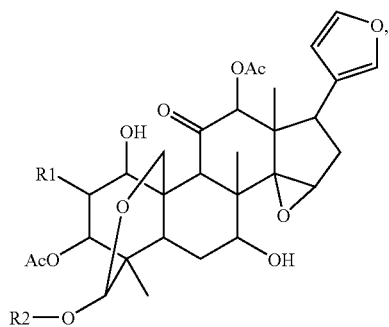

Structure (I)

where R1 comprises H or OAc and R2 comprises H or COCH$(CH_3)_2$; and a pharmaceutically acceptable carrier or salt, wherein the anti-hepatitis C composition is used for inhibiting hepatitis C viruses or treating hepatitis C.

The invention also provides a method for preparing a drug for inhibiting hepatitis C viruses or treating hepatitis C, wherein an effective amount of limonoid compound is used, and the structure of the limonoid compound is shown as Structure (I):

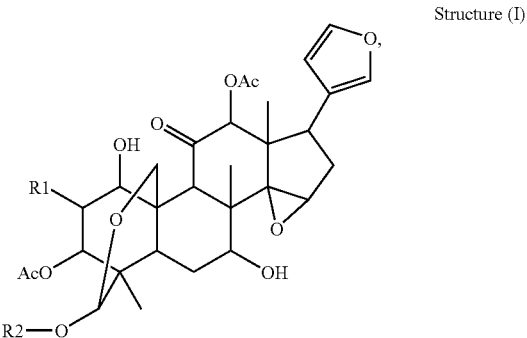

Structure (I)

where R1 comprises H or OAc and R2 comprises H or COCH$(CH_3)_2$.

The invention further provides a method for treating hepatitis C, comprising administering an effective amount of an anti-hepatitis C composition to a patient in need, wherein the anti-hepatitis C composition comprises: an effective amount of limonoid compound, wherein the structure of the limonoid compound is shown as Structure (I):

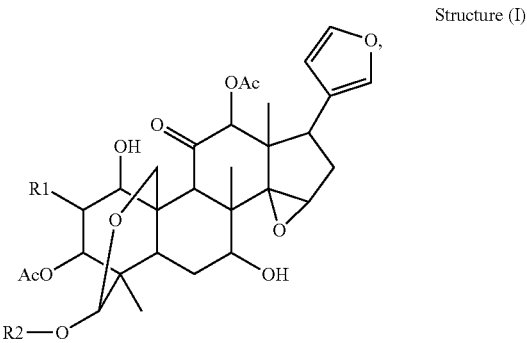

Structure (I)

where R1 comprises H or OAc and R2 comprises H or COCH$(CH_3)_2$; and a pharmaceutically acceptable carrier or salt.

A detailed description is given in the following embodiments with reference to the accompanying drawings.

BRIEF DESCRIPTION OF THE DRAWINGS none

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention uses a composition comprising a limonoid compound as an anti-hepatitis C drug which is used for inhibiting hepatitis C viruses or treating hepatitis C. In one embodiment, the composition may comprise an effective amount of limonoid compound and a pharmaceutically acceptable carrier or salt, and a structure of the limonoid compound is shown as Structure (I):

Structure (I)

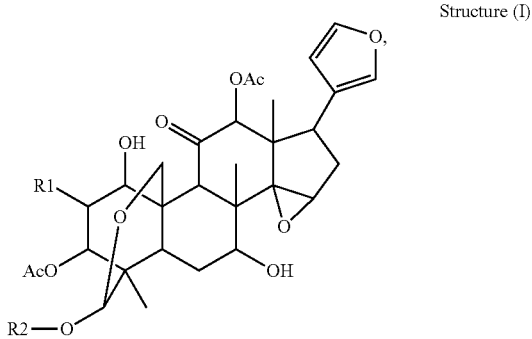

where R1 comprises H or OAc and R2 comprises H or COCH(CH$_3$)$_2$.

Moreover, the limonoid compound may be extracted from a plant material, and the plant material may comprise Melia toosendan Sieb. Et Zucc. or Melia azedarach Linn.

The limonoid compound may comprise toosendanin or Trichilin H. Structures of toosendanin and Trichilin H are shown as Structures (II) and (III), respectively:

Structure (II)

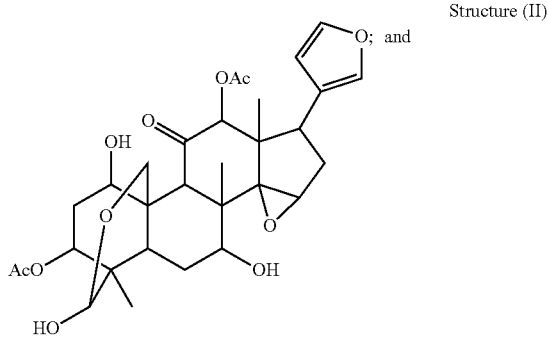

Structure (III)

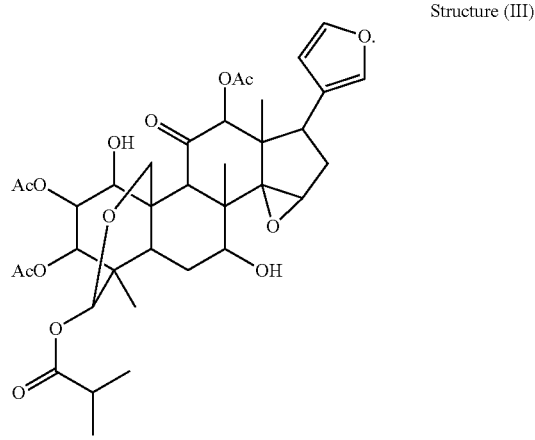

The HCV replicon system has been used worldwide as new drug development tool (V. Lohmann et al., 1999, *Science*. Vol. 285, 110-113; R. Bartenschlager, 2002, *Nature Reviews/Drug Discovery*. Vol. 1, 911-916; J. M. Vorlijk et al., 2003, *Journal of Virological Methods*. 110:201-209). The Huh-luc/neo-ET cell has I389luc-ubi-NS3-3'/ET replicon and could be used to monitor the replicative capability of the HCV. The Huh-luc/neo-ET is able to express a firefly luciferase-ubiquitin-neomycin fusion protein translated by the internal ribosomal entry site (IRES) of the hepatitis C virus and is able to express the hepatitis C viral nonstructural protein (NS3-5B) including protease, helicase and polymerase translated by the IRES of the encephalomyocarditis virus (EMCV). When the replication complex composed of the IRES of the hepatitis C virus or the nonstructural protein of the hepatitis C virus is influenced by a candidate, the effect of the candidate for inhibiting the activity of the hepatitis C virus repilcon can be estimated by determining the intensity of the firefly luciferase activity. The hepatitis C virus inhibition effect of the limonoid compound can be determined by determining the firefly luciferase activity expressed by the Huh-luc/noe-ET cell in presence of the limonoid compound.

In the Huh-luc/neo-ET cell, 50% of the HCV replication inhibition concentration (IC$_{50}$) of the limonoid compound is at least less than about 0.5 µg/ml, preferably about 0.045 µg/ml. Furthermore, the effect window (EW), a ratio of 50% of the cell cytotoxic concentration (CC$_{50}$) to IC$_{50}$, of the limonoid compound is at least greater than about 100, preferably greater than about 2500.

In one embodiment, the limonoid compound may comprise toosendanin Structure of toosendanin is shown as Structure (II):

Structure (II)

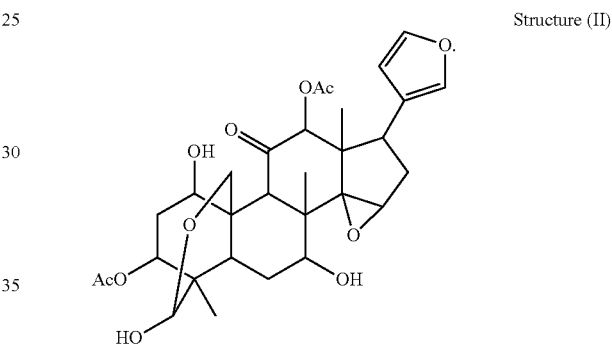

The toosendanin may be extracted from a plant material, and the plant material may comprise Melia toosendan Sieb. Et Zucc. or Melia azedarach Linn. In the Huh-luc/neo-ET cell, the IC$_{50}$ of the toosendanin is at least less than about 0.05 µg/ml, and the EW of the toosendanin is at least greater than about 2500.

In another embodiment, the limonoid compound may comprise Trichilin H. Structure of Trichilin H is shown as Structure (III):

Structure (III)

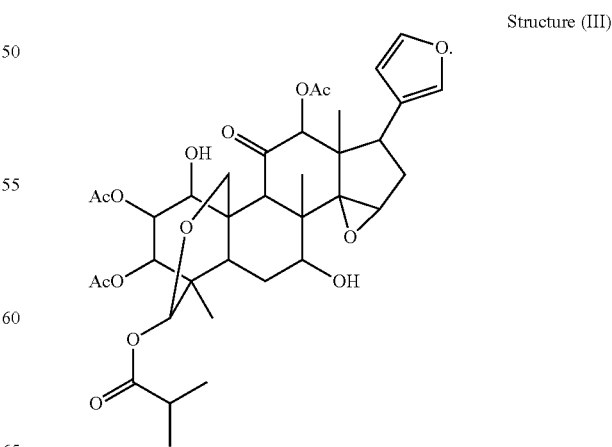

The Trichilin H may be extracted from a plant material, and the plant material may comprise Melia toosendan Sieb. Et Zucc. or Melia azedarach Linn. In the Huh-luc/neo-ET cell, the $IC_{50}$ of the Trichilin H is at least less than about 0.5 μg/ml, and the EW of the Trichilin H is at least greater than about 100.

A pharmaceutically acceptable carrier may comprise, but is not limited to, a solvent, a dispersion medium, a coating, an antibacterial and antifungal agent, or an isotonic and absorption delaying agent. The pharmaceutical composition can be formulated into dosage forms for different administration routes utilizing conventional methods.

The pharmaceutically acceptable salt may comprise, but is not limited to, inorganic cation salts including alkali metal salts such as sodium salt, potassium salt or amine salt, alkaline-earth metal salt such as magnesium salt or calcium salt, the salt containing bivalent or quadrivalent cation such as zinc salt, aluminum salt or zirconium salt. In addition, the pharmaceutically acceptable salt may also comprise organic salt including dicyclohexylamine salt, methyl-D-glucamine, and amino acid salt such as arginine, lysine, histidine, or glutamine.

The pharmaceutical composition may be administered orally, parentally by an inhalation spray or via an implanted reservoir. The parental method may comprise subcutaneous, intracutaneous, intravenous, intramuscular, intraarticular, intraarterial, intrasynovial, intrasternal, intrathecal, and intraleaional, as well as infusion techniques.

An oral composition can comprise, but is not limited to, tablets, capsules, emulsions and aqueous suspensions, dispersions and solutions.

In another aspect, the invention may further provide a method for preparing a drug for inhibiting hepatitis C viruses or treating hepatitis C.

In the method of the invention, an effective amount of limonoid compound is used as an active ingredient for the drug. Structure of the limonoid compound is shown as Structure (I):

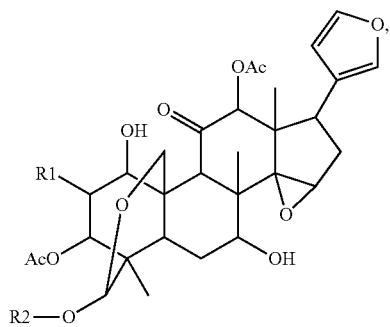

Structure (I)

where R1 comprises H or OAc and R2 comprises H or $COCH(CH_3)_2$.

The limonoid compound may be extracted from a plant material, and the plant material may comprise Melia toosendan Sieb. Et Zucc. or Melia azedarach Linn.

In addition, the limonoid compound may comprise toosendanin or Trichilin H. Structures of toosendanin and Trichilin H are shown as Structures (II) and (III), respectively:

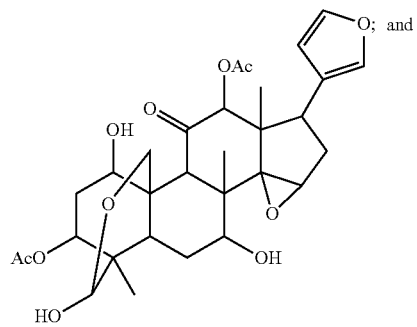

Structure (II)

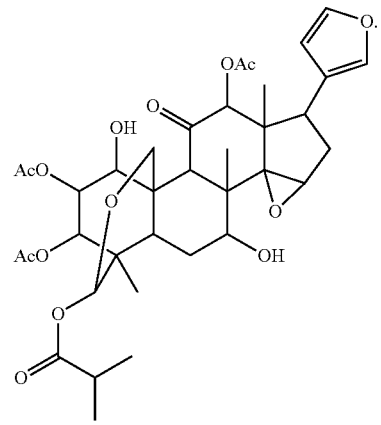

Structure (III)

In further another aspect, the invention may provide a method for treating hepatitis C. The method for treating hepatitis C may comprise administering an effective amount of an anti-hepatitis C composition to a patient in need.

The anti-hepatitis C composition is described as above, which may comprise an effective amount of limonoid compound and a pharmaceutically acceptable carrier or salt.

Structure of the limonoid compound is shown as Structure (I):

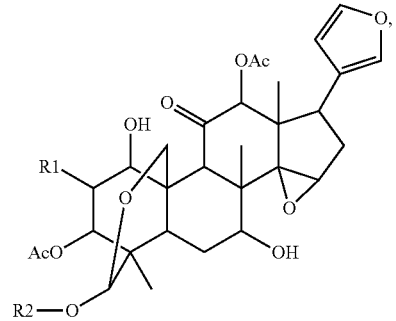

Structure (I)

where R1 comprises H or OAc and R2 comprises H or $COCH(CH_3)_2$.

The limonoid compound may be extracted from a plant material, and the plant material may comprise Melia toosendan Sieb. Et Zucc. or Melia azedarach Linn.

Moreover, the limonoid compound may comprise toosendanin or Trichilin H. Structures of toosendanin and Trichilin H are shown as Structures (II) and (III), respectively:

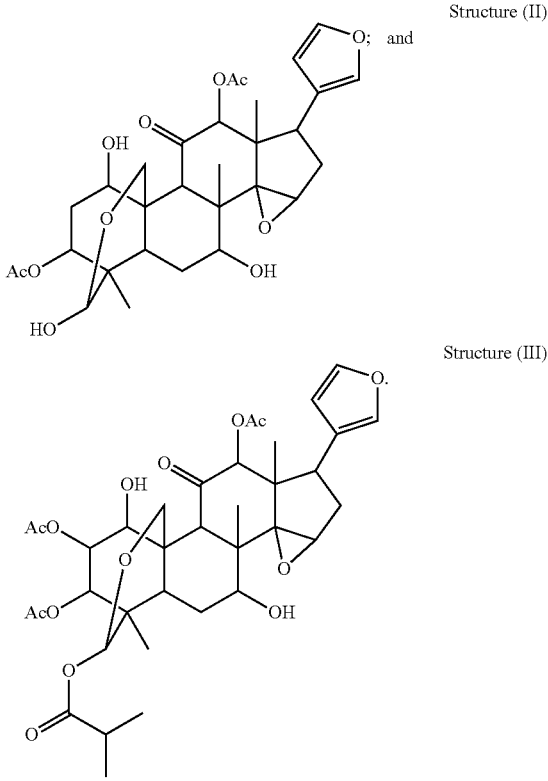

Structure (II) and Structure (III)

Furthermore, the pharmaceutically acceptable carrier and pharmaceutically acceptable salt are described as above.

EXAMPLE

Example 1

Extracting an Effective Ingredient for Inhibiting Hepatitis C Viruses from a Plant Material 5.96 g of chuanlianzi ethanol extract was dissolved in 20 ml of a mixture of methanol and water and extracted with 15 ml of n-hexane, diethyl ether, dichloromethane and ethyl acetate for 2-3 times, respectively to obtain an n-hexane layer extraction solution, diethyl ether layer extraction solution, dichloromethane layer extraction solution and ethyl acetate layer extraction solution, respectively. Each layer extraction solution was concentrated and dried to obtain an n-hexane layer extract, diethyl ether layer extract, dichloromethane layer extract and ethyl acetate layer extract, respectively. The hepatitis C inhibition activity of each layer extract was determined by using a Huh-luc/neo-ET cell (HCV replication system) for testing thereof.

The results showed that the diethyl ether layer extract (1.113 g) had HCV replication inhibition activity. The HCV replication inhibition concentration ($IC_{50}$) thereof was 0.68±0.11 μg/ml.

Open column chromatography was used to isolate 1.1 g of the diethyl ether layer extract with mixtures of n-hexane and acetone with different ratios as a mobile phase and then the diethyl ether layer extract was separated to many fractions. After activity test, the selected fractions containing active ingredients were isolated by a reverse phase semi-preparative HPLC column with water and acetonitrile as a mobile phase and then two compounds were isolated. After that, the NMR spectroscopy and mass spectrometry were used to analyze the two compounds.

The NMR spectral data of the first compound showed that:
$^1$HNMR (500 MHz, CD3OD): 7.39 (s, 1H); 7.19 (s, 1H); 6.16 (s, 1H); 5.34 (s, 1H); 5.20 (s, 1H); 4.71-4.24 (m, 5H); 3.80 (s, 1H); 3.58-3.31 (m, 1H); 2.90-2.54 (m, 4H); 2.19-1.89 (m, 8H); 1.37-1.33 (3H); 1.14-1.11 (3H); 0.84 (s, 3H).

The mass spectral data of the first compound showed that: $ESI^+$-MS: 621[M+2×Na]$^+$; 598[M+Na]$^+$; 558[M−O]$^+$, 498[M−O—OAc]$^+$; 438[M−O−2×OAc]$^+$.

Therefore, the first compound was determined as toosendanin.

Moreover, the NMR spectral data of the second compound showed that:
$^1$HNMR (500 MHz, CD3OD) 7.40 (s, 1H); 7.20 (s, 1H); 6.16 (s, 1H); 5.77 (s, 1H); 5.47 (s, 1H); 5.37 (s, 1H); 5.34 (s, 1H); 4.52 (s, 1H); 4.53-4.31 (m, 2H); 3.82 (s, 1H); 3.578 (m, 1H); 2.96-2.87 (m, 2H); 2.48-2.50 (m, 1H); 2.20 (m, 2H); 2.08 (sm, 2H); 1.99 (s, 3H); 1.93 (s, 3H); 1.90 (s, 3H); 1.34-1.29 (3H); 1.17-1.13 (m, 3H); 0.95-0.88 (m, 6H); 0.83 (s, 3H)

The mass spectral data of the second compound showed that:
$ESI^+$-MS: 749 [M+2×Na]$^+$; 726 [M+Na]$^+$; 635 [M−furan]$^+$; 616 [635−COCH(CH$_3$)$_2$]$^+$; 558 [616−OAc]$^+$.

Therefore, the second compound was determined as Trichilin H.

Example 2

1. Cell Cytotoxic Test of Toosendanin to Huh-luc/noe-ET Cells

Huh-luc/neo-ET cells with concentration of 2.5×10$^4$ cells/100 μl/well were seeded into a 96 well culture plate (Corning Incorporation COSTAR, 3599) and placed into a cell incubator for culturing.

The next day, a toosendanin sample was diluted with a DMEM culture medium to the concentrations of 28.73 μg/ml, 9.57 μg/ml, 3.19 μg/ml, 1.06 μg/ml, 0.35 μg/ml, 0.11 μg/ml, 0.039 μg/ml and 0.013 μg/ml, respectively, or to become the concentrations of 114.92 μg/ml, 38.33 μg/ml, 12.77 μg/ml, 4.25 μg/ml, 1.42 μg/ml, 0.46 μg/ml, 0.16 μg/ml and 0.057 μg/ml, respectively. The initial medium in the 96 well culture plate was sucked out by a vacuum pump (DOAT-704AA) without removing the cells. Then, the toosendanin culture medium with concentrations mentioned above were added into the 96 well culture plate containing cells with amount of 100 μl/well as experiment groups while untreated culture medium were added to the cells as a control group.

After culturing for two days, the medium was removed and each well containing cells of 96 well culture plate was washed twice by 100 μl of 1×PBS (1 mM $KH_2PO_4$, 10 mM $Na_2HPO_4$, 137 mM NaCl, 2.7 mM KCl) and whether there was drug precipitate on the well was observed and recorded. Then, PBS was removed and 50 μl of medium containing MTT (Sigma, M2128) with a concentration of 0.5 mg/ml was added into each well of the 96 well culture plate. After the 96 well culture plate was placed in a $CO_2$ culture incubator for 1 hour, DMSO (Riedel-de Haën, 60153) with amount of 150 μl/well was added into the 96 well culture plate and vortexed by a votexer (KS shaker Type 670) to thoroughly mix the resulting purple precipitate. After the purple precipitate was thoroughly mixed, the 96 well culture plate was placed in a continuous wave length microwell plate analysis system (Molecular Devices, SPECTRAMAX 190) to measure the absorbance of cells at 560 nm.

The average absorbance of the control groups was used as 100% of the cell survival rates (%) to calculate the cell survival rates (%) of the experiment groups with different concentrations of toosendanin samples. The formula of the cell survival rate was: (absorbance of experiment group/absorbance of the control group)×100%. The cell survival rates of all experiment groups were drawn to form an x-y graph and thus a trend line formula with $R^2$ value greater than 0.9 was obtained.

In the trend line formula, when y was 50, the resulting X meant 50% of the cell cytotoxic concentration ($CC_{50}$) or when y was 85, the resulting X meant 15% of the cell cytotoxic concentration ($CC_{15}$). Due to the property of the sample, $CC_{15}$ was calculated from the trend line formula generated by the experiment groups containing samples with concentrations of 3.19 μg/ml, 1.06 μg/ml, 0.35 μg/ml, 0.11 μg/ml and 0.039 μg/ml. The result is shown as Table 1. 50% of the cell cytotoxic concentration ($CC_{50}$) of the toosendanin was greater than 114.8 μg/ml, and 15% of the cell cytotoxic concentration ($CC_{15}$) of the toosendanin was 0.34 μg/ml.

When the cell survival rates (%) was greater than 85%, it meant that the sample at or less than the concentration (the concentration less than $CC_{15}$) was non-cytotoxic. The samples with non-cytotoxic concentrations were selected for a test to be performed for firefly luciferase activity of Huh-luc/neo-ET cells (detailed in the following).

2. Estimating the HCV Replication Inhibition Effect of Toosendanin by Determining the Firefly Luciferase Activity The Huh-luc/neo-ET cells were co-cultured with toosendanin with concentrations of 0.15 μg/ml, 0.075 μg/ml, 0.038 μg/ml, 0.019 μg/ml and 0.0085 μg/ml, respectively for 2 days and then were washed twice by 100 μl of 1×PBS (1 mM KH2PO4, 10 mM Na2HPO4, 137 mM NaCl, 2.7 mM KCl) and PBS was removed. 35 μl of 1× passive lysis buffer (Promega, E1941) was added to the cells and vortexed by a vortexer for 10 minutes to thoroughly mix the cells.

Cell suspension with an amount of 30 μl/well was added to a 96 well white plate(NUNC, 236108) for measuring luciferase activity, and 40 μl/well of luminescence analysis buffer and 20 μl/well of luminescence substrate (1 mM D-Luciferin) were sequentially added into the 96 well white plates. After the substrate was added, a microplate luminescence meter (Berthold, MPL4) was used to measure the luciferase activity (Rlu/s).

The luciferase activity of the control group was used as a standard to calculate the hepatitis C virus inhibition rates (%) of the experiment groups. The formula of inhibition rates (%) was: {[(luciferase activity of control group)−(luciferase activity of experiment group)]/(luciferase activity of control group)}×100%. After the sample was serial diluted and the HCV replication inhibition rates were determined at different concentrations, 50% of the HCV replication inhibition concentration ($IC_{50}$) was calculated by grafit5 software (Erithacus Software).

For each experiment, except for the PEG IFN alpha-2a with concentrations of 0.5 ng/ml and 0.1 ng/ml were used as positive controls for the $IC_{50}$ test. Additionally, cyclosporine A (CsA) with a concentration of 1 μg/ml was also used as a positive control for the $IC_{50}$ test.

The result is shown as Table 1, wherein 50% of the HCV replication inhibition concentration ($IC_{50}$) of the toosendanin was 0.045±0.004 μg/ml, and, 90% of the HCV replication inhibition concentration ($IC_{90}$) of the toosendanin was 0.35 μg/ml.

Example 3

1. Cell Cytotoxic Test of Trichilin H to Huh-luc/neo-ET Cells

The experiment procedure was the same as Example 2 while the testing sample was replaced with Trichilin H. The Trichilin H sample was diluted with a DMEM culture medium to become final concentrations of 50 μg/ml, 25 μg/ml, 8.33 μg/ml, 2.78 μg/ml, 0.93 μg/ml, 0.31 μg/ml, 0.1 μg/ml and 0.03 μg/ml, respectively.

The result is shown as Table 1, wherein 50% of the cell cytotoxic concentration ($CC_{50}$) of the toosendanin was greater than 50 μg/ml, and 15% of the cell cytotoxic concentration ($CC_{15}$) of the toosendanin was 0.7 μg/ml.

2. Estimating the HCV Replication Inhibition Effect of Trichilin H by Determining the Firefly Luciferase Activity The experiment procedure was the same as Example 2 while the testing sample was replaced with Trichilin H. The Huh-luc/neo-ET cells were co-cultured with Trichilin H with concentrations of 0.75 μg/ml, 0.5 μg/ml, 0.25 μg/ml and 0.125 μg/ml, respectively.

The result is shown as Table 1, wherein 50% of the HCV replication inhibition concentration ($IC_{50}$) of the Trichilin H was 0.48±0.10 μg/ml, and 90% of the HCV replication inhibition concentration ($IC_{90}$) of the Trichilin H was 0.9 μg/ml.

TABLE 1

Cell cytotoxic concentration and HCV replication inhibition concentration of the test sample

| Sample | $CC_{50}$ (μg/ml) | $CC_{15}$ (μg/ml) | $IC_{50}$ (μg/ml) | $IC_{90}$ (μg/ml) | EW ($CC_{50}/IC_{50}$) |
|---|---|---|---|---|---|
| Toosendanin | >114 | 0.34 | 0.045 ± 0.004 | 0.35 | >2531.6 |
| Trichilin H | >50 | 0.7 | 0.48 ± 0.10 | 0.9 | >104.2 |

$CC_{50}$: 50% of the cell cytotoxic concentration
$CC_{15}$: 15% of the cell cytotoxic concentration
$IC_{50}$: 50% of the HCV replication inhibition concentration
$IC_{90}$: 90% of the HCV replication inhibition concentration
EW: 50% of the cell cytotoxic concentration/50% of the HCV replication inhibition concentration

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for treating hepatitis C, comprising administering an effective amount of an anti-hepatitis C composition to a patient in need, wherein the anti-hepatitis C composition consists essentially of
a limonoid compound, wherein the structure of the limonoid compound is shown as Structure (I):

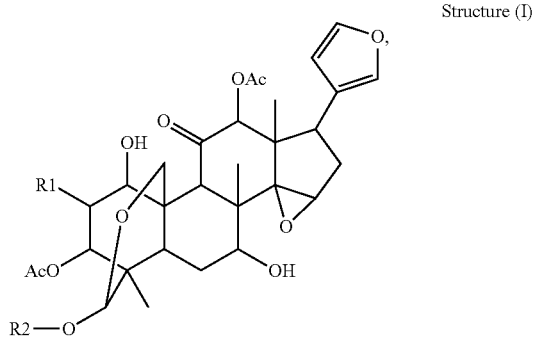

Structure (I)

wherein R1 is H or OAc and R2 is H or COCH(CH$_3$)$_2$; and
a pharmaceutically acceptable carrier or salt.

2. The method for treating hepatitis C as claimed in claim 1, wherein the limonoid compound is extracted from a plant material.

3. The method for treating hepatitis C as claimed in claim 2, wherein the plant material comprises Melia toosendan Sieb. Et Zucc. or Melia azedarach Linn.

4. The method for treating hepatitis C as claimed in claim 1, wherein the limonoid compound comprises toosendanin and a structure of toosendanin is shown as Structure (II):

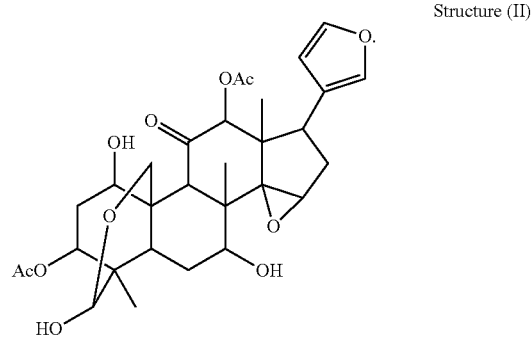

Structure (II)

5. The method for treating hepatitis C as claimed in claim 1, wherein the limonoid compound comprises Trichilin H, and a structure of Trichilin H is shown as Structure (III):

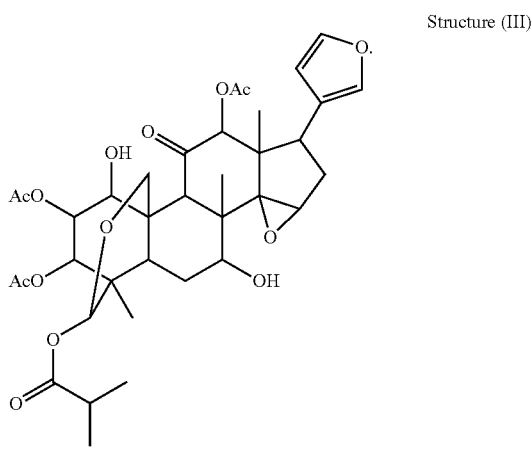

Structure (III)

* * * * *